US012569680B2

(12) United States Patent
 Shrivastav et al.

(10) Patent No.: US 12,569,680 B2
(45) Date of Patent: Mar. 10, 2026

(54) PATIENT USER INTERFACE FOR A STIMULATION/BLOCK THERAPY FOR TREATMENT OF TYPE 2 DIABETES

(71) Applicant: Medtronic, Inc., Minneapolis, MN (US)

(72) Inventors: Maneesh Shrivastav, Blaine, MN (US); ShaileshKumar V. Musley, Brooklyn Park, MN (US); Kanthaiah Koka, Valencia, CA (US); Steven M. Goetz, North Oaks, MN (US); Suryakiran Vadrevu, Santa Clarita, CA (US); Rebecca K. Gottlieb, Culver City, CA (US); David John Miller, Austin, TX (US); Leonid M. Litvak, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 303 days.

(21) Appl. No.: 18/132,219

(22) Filed: Apr. 7, 2023

(65) Prior Publication Data

US 2023/0355969 A1 Nov. 9, 2023

Related U.S. Application Data

(60) Provisional application No. 63/342,998, filed on May 17, 2022, provisional application No. 63/342,967, (Continued)

(51) Int. Cl.
 *A61N 1/36* (2006.01)
 *A61B 5/00* (2006.01)
 (Continued)

(52) U.S. Cl.
 CPC ...... *A61N 1/36053* (2013.01); *A61B 5/14532* (2013.01); *A61B 5/7435* (2013.01);
 (Continued)

(58) Field of Classification Search
 CPC .................................................. A61N 1/36053
 See application file for complete search history.

(56) References Cited

U.S. PATENT DOCUMENTS 5,487,756 A 1/1996 Kallesoe et al.
6,572,543 B1 6/2003 Christopherson et al.
 (Continued)

FOREIGN PATENT DOCUMENTS

CN 101401314 4/2009
WO WO 2017/115368 7/2017
 (Continued)

OTHER PUBLICATIONS

U.S. Appl. No. 18/131,500, filed Apr. 6, 2023.
 (Continued)

*Primary Examiner* — Carl H Layno
*Assistant Examiner* — Bryan Mcallister Lee
(74) *Attorney, Agent, or Firm* — Sheridan Ross P.C.

(57) ABSTRACT

A system is provided herein for stimulating an anatomical element of a patient. For example, a device may be configured to generate a current, and an electrode device coupled to the device may be configured to apply the current to the anatomical element. Additionally, the system may include a user interface in communication with the implantable pulse generator, the electrode device, or both. In some examples, the user interface may include a first element that is configured to display information associated with the patient. Additionally, the user interface may include a second element that is configured to receive inputs for programming parameters of the current. The user interface may also (Continued)

include a third element that is configured to display diagnostic information associated with applying the current to the anatomical element.

20 Claims, 6 Drawing Sheets

Related U.S. Application Data filed on May 17, 2022, provisional application No. 63/342,945, filed on May 17, 2022, provisional application No. 63/339,136, filed on May 6, 2022, provisional application No. 63/339,154, filed on May 6, 2022, provisional application No. 63/339,024, filed on May 6, 2022, provisional application No. 63/339,304, filed on May 6, 2022, provisional application No. 63/339,101, filed on May 6, 2022, provisional application No. 63/339,160, filed on May 6, 2022, provisional application No. 63/339,049, filed on May 6, 2022, provisional application No. 63/338,817, filed on May 5, 2022, provisional application No. 63/338,794, filed on May 5, 2022, provisional application No. 63/338,806, filed on May 5, 2022.

(51) Int. Cl.

| | |
|---|---|
| *A61B 5/145* | (2006.01) |
| *A61B 17/00* | (2006.01) |
| *A61B 17/135* | (2006.01) |
| *A61N 1/02* | (2006.01) |
| *A61N 1/05* | (2006.01) |
| *A61N 1/372* | (2006.01) |
| *G16H 10/40* | (2018.01) |
| *G16H 20/17* | (2018.01) |

(52) U.S. Cl.

CPC .......... *A61B 17/1355* (2013.01); *A61N 1/025* (2013.01); *A61N 1/0507* (2013.01); *A61N 1/0551* (2013.01); *A61N 1/0556* (2013.01); *A61N 1/0558* (2013.01); *A61N 1/36007* (2013.01); *A61N 1/3606* (2013.01); *A61N 1/36132* (2013.01); *A61N 1/36135* (2013.01); *A61N 1/36139* (2013.01); *A61N 1/36146* (2013.01); *A61N 1/36171* (2013.01); *A61N 1/36185* (2013.01); *A61N 1/37247* (2013.01); *G16H 10/40* (2018.01); *G16H 20/17* (2018.01); *A61B 2017/00867* (2013.01); *A61N 1/3605* (2013.01)

(56) References Cited

U.S. PATENT DOCUMENTS

| | | | |
|---|---|---|---|
| 7,069,078 | B2 | 6/2006 | Houben |
| 7,369,897 | B2 | 5/2008 | Boveja et al. |
| 7,702,386 | B2 | 4/2010 | Dobak et al. |
| 7,818,069 | B2 | 10/2010 | Colborn et al. |
| 8,244,347 | B2 | 8/2012 | Lozano |
| 8,340,760 | B2 | 12/2012 | Dobak, III |
| 8,428,719 | B2 | 4/2013 | Napadow |
| 8,868,211 | B2 | 10/2014 | Durand et al. |
| 9,033,969 | B2 | 5/2015 | Azamian et al. |
| 9,833,621 | B2 | 12/2017 | Levine |
| 9,937,344 | B2 | 4/2018 | Starkebaum et al. |
| 9,974,955 | B2 | 5/2018 | Thornton et al. |
| 10,292,596 | B2 * | 5/2019 | Shadforth .............. A61B 6/503 |
| 10,750,994 | B2 | 8/2020 | Annoni et al. |
| 10,856,926 | B2 | 12/2020 | Azamian et al. |
| 11,191,966 | B2 | 12/2021 | Wah |
| 2006/0282145 | A1 | 12/2006 | Caparso et al. |

| | | | |
|---|---|---|---|
| 2008/0039904 | A1 | 2/2008 | Bulkes et al. |
| 2008/0046055 | A1 | 2/2008 | Durand et al. |
| 2008/0154177 | A1 * | 6/2008 | Moubayed ............. G16H 20/17 604/500 |
| 2008/0215101 | A1 | 9/2008 | Rezai et al. |
| 2008/0234780 | A1 | 9/2008 | Smith et al. |
| 2009/0254143 | A1 | 10/2009 | Tweden et al. |
| 2010/0210955 | A1 | 8/2010 | Forsell |
| 2011/0147046 | A1 | 6/2011 | Bonde et al. |
| 2011/0264116 | A1 | 10/2011 | Kocur et al. |
| 2011/0301408 | A1 | 12/2011 | Augarten |
| 2013/0165994 | A1 | 6/2013 | Ternes et al. |
| 2014/0074188 | A1 | 3/2014 | Armstrong et al. |
| 2015/0045850 | A1 | 2/2015 | Bork et al. |
| 2015/0148869 | A1 | 5/2015 | Dorvall, II et al. |
| 2015/0328464 | A1 | 11/2015 | Henry et al. |
| 2016/0114165 | A1 | 4/2016 | Levine et al. |
| 2017/0164876 | A1 | 6/2017 | Hyde et al. |
| 2018/0085580 | A1 | 3/2018 | Perez et al. |
| 2018/0125689 | A1 | 5/2018 | Perez et al. |
| 2018/0303648 | A1 | 10/2018 | Mische |
| 2019/0125227 | A1 | 5/2019 | Koya et al. |
| 2019/0175915 | A1 | 6/2019 | Brill et al. |
| 2019/0192851 | A1 | 6/2019 | Possover |
| 2019/0339224 | A1 | 11/2019 | Bhavaraju et al. |
| 2020/0206496 | A1 | 7/2020 | Meng |
| 2020/0254259 | A1 | 8/2020 | Libbus et al. |
| 2021/0146136 | A1 * | 5/2021 | Waataja ............... A61N 1/0551 |
| 2021/0244949 | A1 | 8/2021 | Soin |
| 2021/0275819 | A1 | 9/2021 | Boor et al. |
| 2021/0290949 | A1 | 9/2021 | Holinski |
| 2022/0193414 | A1 | 6/2022 | Waataja et al. |

FOREIGN PATENT DOCUMENTS

| | | |
|---|---|---|
| WO | WO 2020/214982 | 10/2020 |
| WO | WO 2020/252428 | 12/2020 |
| WO | WO 2021/119741 | 6/2021 |

OTHER PUBLICATIONS

U.S. Appl. No. 18/131,513, filed Apr. 6, 2023.
U.S. Appl. No. 18/131,542, filed Apr. 6, 2023.
U.S. Appl. No. 18/131,555, filed Apr. 6, 2023.
U.S. Appl. No. 18/131,576, filed Apr. 6, 2023.
U.S. Appl. No. 18/131,592, filed Apr. 6, 2023.
U.S. Appl. No. 18/132,186, filed Apr. 7, 2023.
U.S. Appl. No. 18/131,614, filed Apr. 6, 2023.
U.S. Appl. No. 18/132,204, filed Apr. 7, 2023.
U.S. Appl. No. 18/132,232, filed Apr. 7, 2023.
Aune et al. "Diabetes mellitus and the risk of sudden cardiac death: a systematic review and meta-analysis of prospective studies," Nutrition, Metabolism and Cardiovascular Diseases, 2018, vol. 28, pp. 543-556.
Bergner et al. "Diabetes mellitus and sudden cardiac death," Cardiology Journal, 2010, vol. 17, No. 2, pp. 117-129.
Chow et al. "Risk of Cardiac Arrhythmias During Hypoglycemia in Patients with Type 2 Diabetes and Cardiovascular Risk," Diabetes, May 2014, vol. 63, No. 5, pp. 1738-1747.
Hanefeld et al. "Hypoglycemia and Cardiovascular Risk: Is There a Major Link?" Diabetes Care, 2016, vol. 39, Suppl. 2, pages S205-S209.
Hirotani et al. "Carbon Nanotube Thin Films for High-Performance Flexible Electronics Applications," Topics in Current Chemistry, Jan. 2019, vol. 377, No. 1, Article No. 3.
Hsieh et al. "The enigma of the dead-in-bed syndrome: challenges in predicting and preventing this devastating complication of type 1 diabetes," Journal of Diabetes and its Complications, 2014, vol. 28, pp. 585-587.
Jones et al. "Neuromodulation using ultra low frequency current waveform reversibly blocks axonal conduction and chronic pain," Science Translational Medicine, Aug. 2021, vol. 13, No. 608, article eabg9890.
Jovanov et al. "Sensors and Systems for Obesity Care and Research," IEEE, 36th Annual International Conference of the IEEE Engineering in Medicine and Biology Society, Aug. 2014, pp. 3188-3191.

(56)        References Cited

OTHER PUBLICATIONS

Murastov et al. "Flexible and water-stable graphene-based electrodes for long-term use in bioelectronics," Biosensors and Bioelectronics, Oct. 2020, vol. 166, Article 112426.

Shapiro et al. Pudendal Nerve Block by Low-Frequency (≤1 kHz) Biphasic Electrical Stimulation, Neuromodulations, Aug. 2021, vol. 24, No. 6, pp. 1012-1017.

Tancredi et al. "Excess Mortality among Persons with Type 2 Diabetes," The New England Journal of Medicine, 2015, vol. 373, pp. 1720-1732.

Yi et al. "The role of the autonomic nervous liver innervation in the control of energy metabolism," Biochimica et Biophysica Acta, Apr. 2010, vol. 1802, No. 4, pp. 416-431.

Zaccardi et al. "Diabetes mellitus and risk of sudden cardiac death," International Journal of Cardiology, Dec. 2014, vol. 177, No. 2, pp. 535-537.

International Search Report and Written Opinion for International (PCT) Patent Application No. PCT/US2023/065510, dated Jul. 11, 2023 10 pages.

International Search Report and Written Opinion for International (PCT) Patent Application No. PCT/US2023/065428, dated Jul. 20, 2023 12 pages.

International Preliminary Report on Patentability for International (PCT) Patent Application No. PCT/US2023/065510, dated Nov. 14, 2024 7 pages.

International Preliminary Report on Patentability for International (PCT) Patent Application No. PCT/US2023/065428, dated Nov. 14, 2024 8 pages.

Official Action for U.S. Appl. No. 18/131,500, dated May 21, 2025 6 pages Restriction Requirement.

Official Action for U.S. Appl. No. 18/131,500, dated Jul. 28, 2025 10 pages.

Official Action for U.S. Appl. No. 18/131,513, dated Jun. 4, 2025 12 pages.

Official Action for U.S. Appl. No. 18/131,542, dated Jul. 3, 2025 21 pages.

Official Action for U.S. Appl. No. 18/131,555, dated Jul. 24, 2025 6 pages Restriction Requirement.

Official Action for U.S. Appl. No. 18/131,555, dated Aug. 14, 2025 14 pages.

Official Action for U.S. Appl. No. 18/131,576, dated Jun. 20, 2025 22 pages.

Official Action for U.S. Appl. No. 18/131,576, dated Oct. 7, 2025 20 pages.

Official Action for U.S. Appl. No. 18/131,592, dated Jun. 11, 2025 15 pages.

Official Action for U.S. Appl. No. 18/131,592, dated Sep. 19, 2025 19 pages.

Official Action for U.S. Appl. No. 18/132,186, dated Aug. 19, 2025 24 pages.

Official Action for U.S. Appl. No. 18/131,614, dated Sep. 17, 2025 8 pages.

Official Action for U.S. Appl. No. 18/132,232, dated Jul. 17, 2025 20 pages.

* cited by examiner

300

Vagal Nerve Stimulation
Clinician Dashboard

| Patient Info | Programming | Patient Diagnostics |  |

Patient Name │John Doe│

Med Rec No │123456│

Birthdate │11/14/1978│

Implant │02/12/2020│

Clinic │St. Johns Hospital│

Physician │Dr. J Albert ▼│

Labs │Lipid Profile
EKG
Echo
X-Ray│

Gender
◉ Male
○ Female

Clinical Notes

Mr. Doe was diagnosed
with Type 2 diabetes in
April 2016. He met the
indications for implant
and was recommended...

Latest Rhythm

NSR, 01/03/2021

FIG.3

400

Vagal Nerve Stimulation
Clinician Dashboard

| Patient Info | Programming | Patient Diagnostics | ✛ |

Quick Program

Stim Patterns [ Pattern 1 ▼ ]

Waveform [ Square ▼ ]

0.5  0.8      2  3
0.1 ⊖ 1      1 ⊖ 5

Stim Frequency (Hz)    Block Freq (Hz)

[ Emergency Pause ]

Therapy Optimization

[ Download data from IPG ]

[ Run Machine Learning Algo ]

[ IPG Diagnostics ]

[ Run Growth Curves ]

Programming Recommendations

Block Frequency [ 5 KHz ]
Stim Frequency [ 0.8 Hz ]
Waveform [ Square ]

Vagal Nerve Stimulation
Clinician Dashboard

| Patient Info | Programming | Patient Diagnostics | ✚ |

Time Window
- ◉ 24 hours
- ○ 7 days
- ○ 30 days

Device activations [34]
Ave Duration (min) [18]
Ave time: peak to in range [14min]

Time in Range [35%]
Self reported satisfaction [93%]
Current Stim Freq [0.8Hz]
Current Block Freq [5 KHz]

CGM data

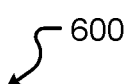
600
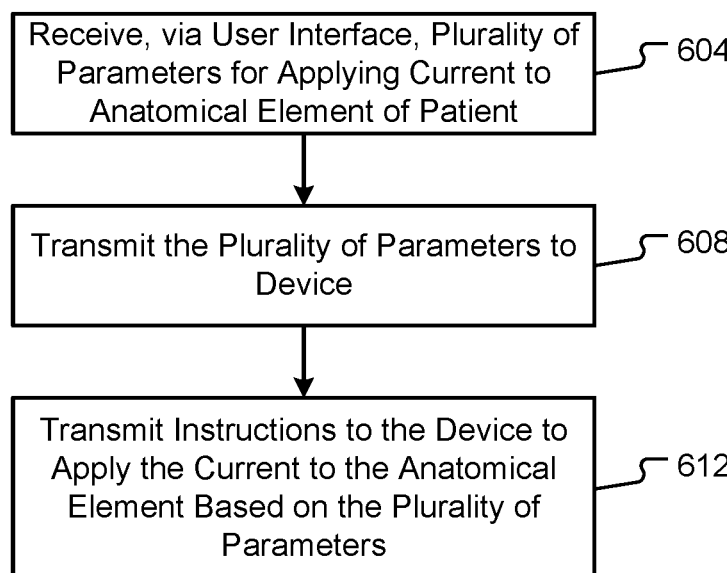
Receive, via User Interface, Plurality of
Parameters for Applying Current to
Anatomical Element of Patient　　604
Transmit the Plurality of Parameters to
Device　　608
Transmit Instructions to the Device to
Apply the Current to the Anatomical
Element Based on the Plurality of
Parameters　　612
FIG. 6

PATIENT USER INTERFACE FOR A STIMULATION/BLOCK THERAPY FOR TREATMENT OF TYPE 2 DIABETES

CROSS REFERENCE TO RELATED APPLICATIONS

This application claims the benefit of U.S. Provisional Application No. 63/342,967, filed on May 17, 2022, entitled "Patient User Interface for a Stimulation/Block Therapy for Treatment of Type 2 Diabetes"; U.S. Provisional Application No. 63/338,794, filed on May 5, 2022, entitled "Systems and Methods for Stimulating an Anatomical Element Using an Electrode Device"; U.S. Provisional Application No. 63/339,049, filed on May 6, 2022, entitled "Systems and Methods for Mechanically Blocking a Nerve"; U.S. Provisional Application No. 63/338,806, filed on May 5, 2022, entitled "Systems and Methods for Wirelessly Stimulating or Blocking at Least One Nerve"; U.S. Provisional Application No. 63/339,101, filed on May 6, 2022, entitled "Neuromodulation Techniques to Create a Nerve Blockage with a Combination Stimulation/Block Therapy for Glycemic Control"; U.S. Provisional Application No. 63/339,136, filed on May 6, 2022, entitled "Neuromodulation for Treatment of Neonatal Chronic Hyperinsulinism"; U.S. Provisional Application No. 63/342,945, filed on May 17, 2022, entitled "Neuromodulation Techniques for Treatment of Hypoglycemia"; U.S. Provisional Application No. 63/342,998, filed on May 17, 2022, entitled "Closed-Loop Feedback and Treatment"; U.S. Provisional Application No. 63/338,817, filed on May 5, 2022, entitled "Systems and Methods for Monitoring and Controlling an Implantable Pulse Generator"; U.S. Provisional Application No. 63/339,024, filed on May 6, 2022, entitled "Programming and Calibration of Closed-Loop Vagal Nerve Stimulation Device"; U.S. Provisional Application No. 63/339,304, filed on May 6, 2022, entitled "Systems and Methods for Stimulating or Blocking a Nerve Using an Electrode Device with a Sutureless Closure"; U.S. Provisional Application No. 63/339,154, filed on May 6, 2022, entitled "Personalized Machine Learning Algorithm for Stimulation/Block Therapy for Treatment of Type 2 Diabetes"; and U.S. Provisional Application No. 63/339,160, filed on May 6, 2022, entitled "Utilization of Growth Curves for Optimization of Type 2 Diabetes Treatment", all of which applications are incorporated herein by reference in their entireties.

BACKGROUND

The present disclosure is generally directed to therapeutic neuromodulation and relates more particularly to a stimulation/block therapy to affect glycemic control of a patient.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic.

BRIEF SUMMARY

Example aspects of the present disclosure include:

A system for stimulating an anatomical element of a patient, comprising: an implantable pulse generator configured to generate a current; an electrode device electrically coupled to the implantable pulse generator, the electrode device comprising a plurality of electrodes configured for placement on or around the anatomical element of the patient; a user interface in communication with the implantable pulse generator, the electrode device, or both, wherein the user interface comprises a first element configured to display information associated with the patient, a second element configured to receive inputs for programming parameters of the current, and a third element configured to display diagnostic information associated with applying the current to the anatomical element; a processor; and a memory storing data for processing by the processor, the data, when processed, causes the processor to: transmit instructions to the implantable pulse generator to apply the current to the anatomical element of the patient via the plurality of electrodes of the electrode device based at least in part on one or more inputs entered via the user interface, wherein the current is configured to adjust glucose levels in the patient when applied to the anatomical element.

Any of the aspects herein, wherein the anatomical element comprises a celiac vagal trunk and a hepatic vagal trunk of the patient.

Any of the aspects herein, wherein the first element of the user interface comprises: a plurality of editable fields configured for entering a name of the patient, a gender of the patient, a medical record number associated with the patient, a birthdate of the patient, a date that the implantable pulse generator is implanted in the patient, a clinic name associated with the patient, a name of a physician associated with the patient, notes from a clinician, or a combination thereof, and a selectable window comprising a plurality of laboratory test options associated with the patient.

Any of the aspects herein, wherein the memory stores further data for processing by the processor that, when processed, causes the processor to: receive a selection of a first laboratory test from the plurality of laboratory test options in the selectable window; retrieve, via a database storing results associated with each of the plurality of laboratory test options for the patient, results of the first laboratory test for the patient based at least in part on the received selection; and display the retrieved results of the first laboratory test within the first element of the user interface.

Any of the aspects herein, wherein the second element of the user interface comprises: a plurality of selectable parameters for configuring how the current is to be applied to the anatomical element, wherein the plurality of selectable parameters comprises a stimulation pattern, a waveform of the current, a stimulation frequency, a block frequency, or a combination thereof, a plurality of buttons associated with determining optimizations for applying the current to the anatomical element to achieve a desired glycemic response in the patient, wherein the plurality of buttons comprises a first button for downloading data from the implantable pulse generator, a second button for running a machine learning algorithm configured to determine optimal parameters for applying the current, a third button for running a diagnostic test of the implantable pulse generator, and a fourth button for generating a set of growth curves associated with applying the current to the anatomical element; a feedback window configured to display recommended parameters for applying the current to the anatomical element, wherein the recommended parameters are displayed based at least in part on a user interacting with the second button for running the machine learning algorithm configured to determine the optimal parameters; and an emergency pause button that, when selected by a user, is configured to initiate a stopping procedure, wherein the stopping procedure comprises stopping a neuromodulation therapy that includes applying the current to the anatomical element.

Any of the aspects herein, wherein the memory stores further data for processing by the processor that, when processed, causes the processor to: receive a plurality of parameters for applying the current to the anatomical element based at least in part on the plurality of selectable parameters; and transmit the received plurality of parameters to the implantable pulse generator, wherein the current is applied to the anatomical element according to the plurality of parameters.

Any of the aspects herein, wherein the plurality of parameters corresponds to the recommended parameters displayed in the feedback window.

Any of the aspects herein, wherein the memory stores further data for processing by the processor that, when processed, causes the processor to: receive an input corresponding to the user selecting the emergency pause button to initiate the stopping procedure; and transmit instructions to the implantable pulse generator to stop the neuromodulation therapy based at least in part on receiving the input.

Any of the aspects herein, wherein the third element of the user interface comprises: a window comprising a plurality of selectable time windows; a plurality of fields displaying the diagnostic information associated with applying the current to the anatomical element, wherein the diagnostic information comprises information associated with a duty cycle of applying the current to the anatomical element, efficacy measures of how applying the current to the anatomical element achieves a desired glycemic response in the patient, and other measures related to glycemic control; and a graphical display configured to display data associated with glucose measurements received from the patient.

Any of the aspects herein, wherein the memory stores further data for processing by the processor that, when processed, causes the processor to: receive a time window selection from the plurality of selectable time windows; generate the diagnostic information to display in the plurality of fields based at least in part on the time window selection; and display the generated diagnostic information in the plurality of fields.

Any of the aspects herein, further comprising: a monitoring device configured to continuously monitor glucose levels in the patient, wherein the data associated with glucose measurements displayed in the graphical display are generated based at least in part on measurements captured by the monitoring device.

Any of the aspects herein, wherein the user interface is run on a user equipment (UE) that is accessible by the patient, a clinician, or both.

A system for stimulating an anatomical element of a patient, comprising: an implantable pulse generator configured to generate a current; an electrode device comprising: a body and a plurality of electrodes disposed on the body and configured to apply the current to the anatomical element; a user interface in communication with the implantable pulse generator, the electrode device, or both, wherein the user interface comprises a first element configured to display information associated with the patient, a second element configured to receive inputs for programming parameters of the current, and a third element configured to display diagnostic information associated with applying the current to the anatomical element; a processor; and a memory storing data for processing by the processor, the data, when processed, causes the processor to: transmit instructions to the implantable pulse generator to apply the current to the anatomical element of the patient via the plurality of electrodes of the electrode device based at least in part on one or more inputs entered via the user interface, wherein the current is configured to adjust glucose levels in the patient when applied to the anatomical element.

Any of the aspects herein, wherein the anatomical element comprises a celiac vagal trunk and a hepatic vagal trunk of the patient.

Any of the aspects herein, wherein the first element of the user interface comprises: a plurality of editable fields configured for entering a name of the patient, a gender of the patient, a medical record number associated with the patient, a birthdate of the patient, a date that the implantable pulse generator is implanted in the patient, a clinic name associated with the patient, a name of a physician associated with the patient, notes from a clinician, or a combination thereof; and a selectable window comprising a plurality of laboratory test options associated with the patient.

Any of the aspects herein, wherein the second element of the user interface comprises: a plurality of selectable parameters for configuring how the current is to be applied to the anatomical element, wherein the plurality of selectable parameters comprises a stimulation pattern, a waveform of the current, a stimulation frequency, a block frequency, or a combination thereof, a plurality of buttons associated with determining optimizations for applying the current to the anatomical element to achieve a desired glycemic response in the patient, wherein the plurality of buttons comprises a first button for downloading data from the implantable pulse generator, a second button for running a machine learning algorithm configured to determine optimal parameters for applying the current, a third button for running a diagnostic test of the implantable pulse generator, and a fourth button for generating a set of growth curves associated with applying the current to the anatomical element; a feedback window configured to display recommended parameters for applying the current to the anatomical element, wherein the recommended parameters are displayed based at least in part on a user interacting with the second button for running the machine learning algorithm configured to determine the optimal parameters; and an emergency pause button that, when selected by a user, is configured to initiate a stopping procedure, wherein the stopping procedure comprises stopping a neuromodulation therapy that includes applying the current to the anatomical element.

Any of the aspects herein, wherein the third element of the user interface comprises: a window comprising a plurality of selectable time windows; a plurality of fields displaying the diagnostic information associated with applying the current to the anatomical element, wherein the diagnostic information comprises information associated with a duty cycle of applying the current to the anatomical element, efficacy measures of how applying the current to the anatomical element achieves a desired glycemic response in the patient, and other measures related to glycemic control; and a graphical display configured to display data associated with glucose measurements received from the patient.

Any of the aspects herein, wherein the user interface is run on a user equipment (UE) that is accessible by the patient, a clinician, or both.

A system for stimulating an anatomical element of a patient, comprising: an implantable pulse generator configured to generate a current, wherein the current is configured to adjust glucose levels in the patient when applied to the anatomical element; an electrode device electrically coupled to the implantable pulse generator, the electrode device comprising a plurality of electrodes configured for placement on or around the anatomical element of the patient; and a user interface in communication with the implantable pulse generator, the electrode device, or both, wherein the user interface comprises a first element configured to display information associated with the patient, a second element configured to receive inputs for programming parameters of the current, and a third element configured to display diagnostic information associated with applying the current to the anatomical element.

Any of the aspects herein, wherein the anatomical element comprises a celiac vagal trunk and a hepatic vagal trunk of the patient.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 3 is a first element of a user interface according to at least one embodiment of the present disclosure;

FIG. 4 is a second element of a user interface according to at least one embodiment of the present disclosure;

FIG. 6 is a flowchart according to at least one embodiment of the present disclosure.

DETAILED DESCRIPTION

Figure 1:
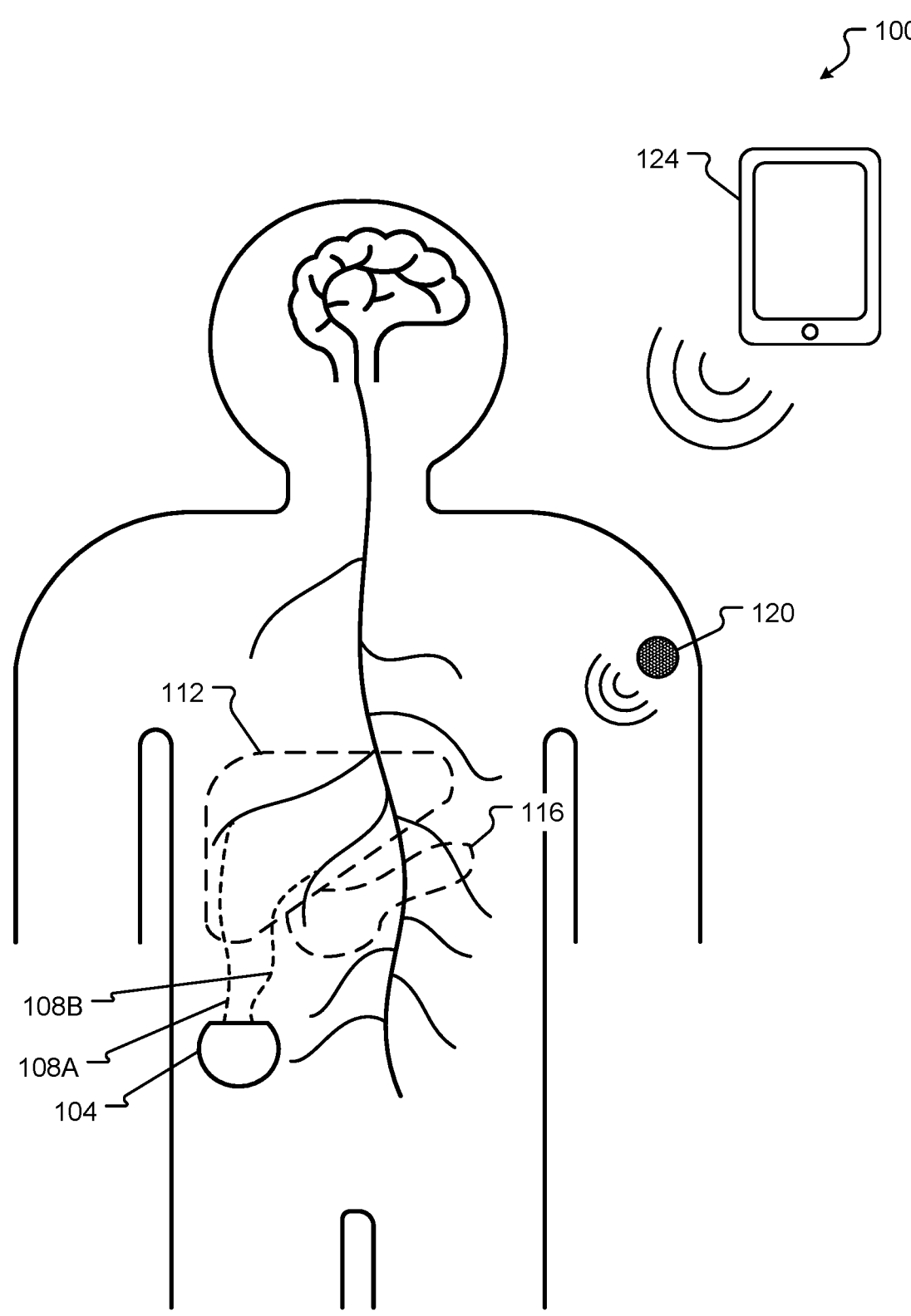
FIG. 1 is a diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., random-access memory (RAM), read-only memory (ROM), electrically erasable programmable ROM (EEPROM), flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 6000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements. The processors listed herein are not intended to be an exhaustive list of all possible processors that can be used for implementation of the described techniques, and any future iterations of such chips, technologies, or processors may be used to implement the techniques and embodiments of the present disclosure as described herein.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Vagus nerve stimulation (VNS) is a technology that has been developed to treat different disorders or ailments of a patient, such as epilepsy and depression. In some examples, VNS involves placing a device in or on a patient's body that uses electrical impulses to stimulate the vagus nerve. For example, the device may be usually placed under the skin of the patient, where a wire (e.g., lead) and/or electrode connects the device to the vagus nerve. Once the device is activated, the device sends signals through the vagus nerve to the patient's brainstem (e.g., or different target area in the patient, such as other organs of the patient), transmitting information to their brain. For example, with VNS, the device may be configured to send regular, mild pulses of electrical energy to the brain via the vagus nerve. In some examples, the device may be referred to as an implantable pulse generator. An implantable vagus nerve stimulator has been approved to treat epilepsy and depression in qualifying patients.

The vagus nerve (e.g., also called the pneumogastric nerve, vagal nerve, the cranial nerve X, etc.) is responsible for various internal organ functions of a patient, including digestion, heart rate, breathing, cardiovascular activity, and reflex actions (e.g., coughing, sneezing, swallowing, and vomiting). Most patients may have one vagus nerve on each side of their body, with numerous branches running from their brainstem through their neck, chest, and abdomen down to part of their colon. The vagus nerve plays a role in many bodily functions and may form a link between different areas of the patient, such as the brain and the gut. The vagus nerve is a critical nerve for supplying parasympathetic information to the visceral organs of the respiratory, digestive, and urinary systems. Additionally, the vagus nerve is important in the control of heart rate, bronchoconstriction, and digestive processes. In some cases, the vagus nerve may be considered a mixed nerve based on including both afferent (sensory) fibers and efferent (motor) fibers. As such, based on including the two types of fibers, the vagus nerve may be responsible for carrying motor signals to organs for innervating the organs (e.g., via the efferent fibers), as well as carrying sensory information from the organs back to the brain (e.g., via the afferent fibers).

The vagus nerve has a number of different functions. Four key functions of the vagus nerve are carrying sensory signals, carrying special sensory signals, providing motor functions, and assisting in parasympathetic functions. For example, the sensory signals carried by the vagus nerve may include signaling between the brain and the throat, heart, lungs, and abdomen. The special sensory signals carried by the vagus nerve may provide signaling of special senses in the patient, such as the taste sensation behind the tongue. Additionally, the vagus nerve may enable certain motor functions of the patient, such as providing movement functions for muscles in the neck responsible for swallowing and speech. The parasympathetic functions provided by the vagus nerve may include digestive tract, respiration, and heart rate functioning. In some cases, the nervous system can be divided into two areas: sympathetic and parasympathetic. The sympathetic side increases alertness, energy, blood pressure, heart rate, and breathing rate. The parasympathetic side, which the vagus nerve is heavily involved in, decreases alertness, blood pressure, and heart rate, and helps with calmness, relaxation, and digestion.

VNS is considered a type of neuromodulation (e.g., a technology that acts directly upon nerves of a patient, such as the alteration, or "modulation," of nerve activity by delivering electrical impulses or pharmaceutical agents directly to a target area). For example, as described above, VNS may include using a device (e.g., implanted in a patient or attached to the patient) that is configured to send regular, mild pulses of electrical energy to a target area of the patient (e.g., brainstem, organ, etc.) via the vagus nerve. The electrical pulses or impulses may affect how that target area of the patient functions to potentially treat different disorders or ailments of a patient.

In some examples, for epileptic patients that suffer from seizures, VNS may change how brain cells work by applying electrical stimulation to certain areas involved in seizures. For example, research has shown that VNS may help control seizures by increasing blood flow in key areas, raising levels of some brain substances (e.g., neurotransmitters) important to control seizures, changing electroencephalogram (EEG) patterns during a seizure, etc. As an example, an epileptic patient's heart rate may increase during a seizure or epileptic episode, so the VNS device may be programmed to send stimulation to the vagus nerve regular intervals and when periods of increased heart rate are seen, where applying stimulation at those times of increased heart rate may help stop seizures. Additionally or alternatively, depression has been tied to an imbalance in certain brain chemicals (e.g., neurotransmitters), so VNS is believed to assist in treating patients diagnosed with depression by using electricity (e.g., electrical pulses/impulses) to influence the production of those brain chemicals.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic. Additionally, in a financial sense, global expenditures for type 2 diabetes treatments, preventive measures, and resulting consequences are estimated at about $966 billion per year. Compounding this issue of high global expenditures is the increasing price of insulin.

As described herein, a neuromodulation technique is provided for glycemic control (e.g., as a treatment for diabetes) using a stimulation/block therapy (e.g., type of VNS). For example, the neuromodulation technique may generally include using a device (e.g., including at least an implantable pulse generator) to provide electrical stimulation (e.g., electrical pulses/impulses) on one or more trunks of the vagus nerve (e.g., vagal trunks) to mute a glycemic response for patients with diabetes. The "patient" as used herein may refer to *Homo sapiens* or any other living being that has a vagus nerve.

In some examples, the device may provide stimulation/blocking of the celiac and hepatic vagal trunks (e.g., using the device) for the purposes of glycemic control. For example, the anterior sub diaphragmatic vagal trunk at the hepatic branching point of the vagus nerve may be electrically blocked (e.g., down-regulated) by delivering a high frequency stimulation (e.g., of about 5 kilohertz (kHz) or in a range between 1 kHz to 50 kHz). Additionally or alternatively, the posterior sub diaphragmatic vagal trunk at the celiac branching point of the vagus nerve may be electrically stimulated (e.g., up-regulated) by delivering a low frequency stimulation (e.g., a square wave at 1 Hz or within a range from 0.1 to 20 Hz). In some examples, the electrical blocking and/or electrical stimulating of the respective vagal trunks may be performed by using one or more cuff electrodes (e.g., of the device) placed on the corresponding vagal trunks (e.g., sutured or otherwise held in place). The desired response by providing the stimulation/block therapy is a muting of the glycemic response of a patient. In some examples, muting of the glycemic response may refer to a lower post prandial peak of the glycemic response as compared to a peak without the stimulation/block therapy being applied.

Using the stimulation/block therapy to achieve a muting of the glycemic response is advantageous for those with type 2 diabetes where the postprandial glycemic response (e.g., occurring after a meal) can be very high. For example, some patients with type 2 diabetes may have high blood sugar levels (e.g., glucose levels) after eating a meal based on their reduced or lack of insulin production (e.g., normal insulin production in the body lowers blood sugar levels postprandially by promoting absorption of glucose from the blood into different cells). Additionally or alternatively, patients diagnosed with type 2 diabetes may generally have high glycemic levels at different points of the day (e.g., not necessarily postprandially or immediately after a meal). Over time, the effect of high glycemic values can have a detrimental effect on one's health, leading to neuropathy, retinopathy, and other ailments. Accordingly, by using the stimulation/block therapy provided herein, a high glycemic response experienced by type 2 diabetes patients may be muted (e.g., the glycemic response is reduced, particularly post prandially). Additionally, the therapy aims to improve insulin sensitivity by blocking hepatic glucose production and also by stimulating pancreatic insulin production needed for glycemic control, where the lack of insulin sensitivity can potentially lead to an imbalance in glycemic control and consequent systemic complications in patients with type 2 diabetes. In some examples, the therapy may also improve fasting hyperglycemia, which can be commonly seen in patients with type 2 diabetes.

In some examples, a user interface may be provided that allows for a clinician and/or a patient to interact with the device (e.g., implantable pulse generator, implantable neurostimulator, etc.) configured to provide the stimulation/blocking of the celiac and hepatic vagal trunks and become involved in the corresponding neuromodulation therapy. The user interface may enable the clinician and/or patient to: 1) view basic patient information, 2) program the device, and 3) view patient diagnostics that can assist in programming. Additionally, the user interface may enable the clinician and/or patient to interrogate the device such that the device can be programmed with therapy information and data can be downloaded from the device. In some examples, the user interface may be intended to be run on a user equipment (UE) device, such as a tablet, a smartphone, a laptop, or another device not explicitly listed herein. Additionally or alternatively, the user interface may be run on equipment owned by an institution, such as a hospital or clinic. Additionally, the user interface may be based on a tabbed scheme with elements corresponding to the different aspects described above. For example, the user interface may include a first tab/element for viewing the patient information, a second tab/element for programming the device, and a third tab/element for viewing the patient diagnostics.

The first tab/element for viewing patient information may include basic information about the patient (e.g., date the device was implanted in the patient, a medical record number for the patient, etc.), as well as information about latest lab results taken for the patient that are available in a clickable fashion. When an element is clicked (e.g., one of the lab results is selected), a lower right area of the first tab/element on the user interface may display the information, where the information is stored in and retrieved from a central database. The first tab/element may also include a space for the clinician to write and save notes associated with the patient.

The second tab/element for programming the device may include basic parameters of the current to be applied to the anatomical element that can be programmed, such as a stimulation pattern, a waveform of interest (e.g., square, trapezoid, sinusoidal, etc.), a stimulation frequency, and a block frequency. Additionally, the second tab/element may include a button group that allows for information download (e.g., from the device), running a machine learning optimization algorithm to determine optimal parameters for applying the current (e.g., to achieve a desired glycemic response), diagnosing technical matters with the device, running a growth curve routine, or a combination thereof. Additionally, an end result of the optimization may be shown in a bottom right area of the second tab/element (e.g., based on the machine learning optimization algorithm).

The third tab/element for viewing patient diagnostics may display basic diagnostic information about the neuromodulation therapy. For example, the diagnostic information may include duty cycle information, efficacy measures of the neuromodulation therapy, and other measures related to glycemic control. Additionally, the third tab may include a number of diagnostic views that integrate information from other devices related to the neuromodulation therapy, such as a continuous glucose monitor. In some examples, the diagnostic views displayed on the third tab can be customizable (e.g., time period for display, for example, can be on the order of hours or days). While the user interface is described herein as including three tabs/elements, the user interface may include a different number of tabs/elements than three.

Embodiments of the present disclosure provide technical solutions to one or more of the problems of (1) providing personalized control of a neuromodulation therapy for a clinician and a patient, (2) providing diagnostic information for determining optimal parameters for the neuromodulation therapy, and (3) providing user-friendly interfaces for interacting with a device configured to apply the neuromodulation therapy.

Turning to FIG. 1, a diagram of a system 100 according to at least one embodiment of the present disclosure is shown. The system 100 may be used to provide glycemic control for a patient and/or carry out one or more other aspects of one or more of the methods disclosed herein. For example, the system 100 may include at least a device 104 that is capable of providing a stimulation/blocking therapy that mutes a glycemic response for patients with diabetes. In some examples, the device 104 may be referred to as an implantable pulse generator, an implantable neurostimulator, or another type of device not explicitly listed or described herein. Additionally, the system 100 may include one or more wires 108 (e.g., leads) that provide a connection between the device 104 and nerves of the patient for enabling the stimulation/blocking therapy.

As described previously, neuromodulation techniques (e.g., technologies that act directly upon nerves of a patient, such as the alteration, or "modulation," of nerve activity by delivering electrical impulses or localized pharmaceutical agents directly to a target area) may be used for assisting in treatments for different diseases, disorders, or ailments of a patient, such as epilepsy and depression. Accordingly, as described herein, the neuromodulation techniques may be used for muting a glycemic response in the patient to assist in the treatment of diabetes for the patient. For example, the device 104 may provide electrical stimulation to one or more trunks of the vagus nerve of the patient (e.g., via the one or more wires 108) to provide the stimulation/blocking therapy for supporting glycemic control in the patient.

In some examples, the one or more wires 108 may include at least a first wire 108A and a second wire 108B connected to respective vagal trunks (e.g., different trunks of the vagus nerve). As described previously, most patients have one vagus nerve on each side of their body, running from their brainstem through their neck, chest, and abdomen down to part of their colon. The vagus nerve plays a role in many bodily functions and may form a link between different areas of the patient, such as the brain and the gut. For example, the vagus nerve is responsible for various internal organ functions of a patient, including digestion, heart rate, breathing, cardiovascular activity, and reflex actions (e.g., coughing, sneezing, swallowing, and vomiting).

Accordingly, the first wire 108A may be connected to a first vagal trunk of the patient (e.g., the anterior sub diaphragmatic vagal trunk at the hepatic branching point of the vagus nerve) to provide an electrical blocking signal (e.g., a down-regulating signal) from the device 104 to that first vagal trunk (e.g., by delivering a high frequency stimulation, such as a given waveform at about 5 kHz). Additionally or alternatively, the second wire 108B may be connected to a second vagal trunk of the patient (e.g., the posterior sub diaphragmatic vagal trunk at the celiac branching point of the vagus nerve) to provide an electrical stimulation signal (e.g., an up-regulating signal) from the device 104 to that second vagal trunk (e.g., by delivering a low frequency stimulation, such as a square wave or other waveform at 1 Hz). By providing the electrical blocking signal and the electrical stimulation signal to the respective vagal trunks, the system 100 may provide a muting of the glycemic response of the patient when the stimulation/blocking therapy is applied. For example, muting of the glycemic response may refer to a lower post prandial peak of the glycemic response as compared to a peak without the stimulation/block therapy being applied.

In some examples, the vagal trunks to which the wires 108 are connected may be connected to or otherwise in the vicinity of one or more organs of the patient, such that the blocking/stimulation signals provided to the respective vagal trunks by the wires 108 and the device 104 are delivered to the one or more organs. For example, the first vagal trunk (e.g., to which the first wire 108A is connected) may be connected to a first organ 112 of the patient, and the second vagal trunk (e.g., to which the second wire 108B is connected) may be connected to a second organ 116. Additionally or alternatively, while the respective vagal trunks are shown as being connected to the corresponding organs of the patient as described, the vagal trunks to which the wires 108 are connected may be connected to the other organ (e.g., the first vagal trunk is connected to the second organ 116 and the second vagal trunk is connected to the first organ 112) or may be connected to different organs of the patient. In some examples, the first organ 112 may represent a liver of the patient, and the second organ 116 may represent a pancreas of the patient. In such examples, the blocking/stimulation signals provided by the wires 108 and the device 104 may be delivered to the liver and/or pancreas of the patient to mute a glycemic response of the patient as described herein.

In some examples, the wires 108 may provide the electrical signals to the respective vagal trunks via electrodes of an electrode device (e.g., cuff electrodes) that are connected to the vagal trunks (e.g., sutured in place, wrapped around the nerves of the vagal trunks, etc.). In some examples, the wires 108 may be referenced as cuff electrodes or may otherwise include the cuff electrodes (e.g., at an end of the wires 108 not connected or plugged into the device 104). Additionally or alternatively, while shown as physical wires that provide the connection between the device 104 and the one or more vagal trunks, the cuff electrodes may provide the electrical blocking and/or stimulation signals to the one or more vagal trunks wirelessly (e.g., with or without the device 104).

Additionally, while not shown, the system 100 may include one or more processors (e.g., one or more DSPs, general purpose microprocessors, graphics processing units, ASICs, FPGAs, or other equivalent integrated or discrete logic circuitry) that are programmed to carry out one or more aspects of the present disclosure. In some examples, the one or more processors may include a memory or may be otherwise configured to perform the aspects of the present disclosure. For example, the one or more processors may provide instructions to the device 104, the cuff electrodes, or other components of the system 100 not explicitly shown or described with reference to FIG. 1 for providing the stimulation/blocking therapy to promote glycemic control in a patient as described herein. In some examples, the one or more processors may be part of the device 104 or part of a control unit for the system 100 (e.g., where the control unit is in communication with the device 104 and/or other components of the system 100).

In some examples, the system 100 may also optionally include a glucose sensor 120 that communicates (e.g., wirelessly) with other components of the system 100 (e.g., the device 104, the one or more processors, etc.) to achieve better glycemic control in the patient. For example, the glucose sensor 120 may continuously monitor glucose levels of the patient, such that if the glucose sensor 120 determines glucose levels are outside a normal or desired range for the patient (e.g., glucose levels are too high or too low in the patient), the glucose sensor 120 may communicate that glucose levels are outside the normal or desired range to the device 104 (e.g., via the one or more processors) to signal for the device 104 to apply the stimulation/blocking therapy described herein to adjust glucose levels in the patient (e.g., mute the glycemic response to lower glucose levels in the patient, block insulin production in the patient as a possible technique to raise glucose levels in the patient, etc.).

Additionally, the system 100 may include a user interface 124 in communication with the device 104, the electrode device (e.g., the cuff electrodes), or both. In some examples, the device 104 may apply the current for the stimulation/blocking therapy based on one or more inputs entered via the user interface 124. For example, the user interface 124 may include a first element configured to display information associated with the patient, a second element configured to receive inputs for programming parameters of the current, and a third element configured to display diagnostic information associated with applying the current for the stimulation/blocking therapy. The first element is described in greater detail with reference to FIG. 3, the second element is described in greater detail with reference to FIG. 4, and the third element is described in greater detail with reference to FIG. 5. Additionally, while the user interface 124 is described herein as including three elements, the user interface 124 may include a different number of elements than three.

The system 100 or similar systems may be used, for example, to carry out one or more aspects of any of the methods described herein. The system 100 or similar systems may also be used for other purposes. Additionally, it will be appreciated that the human body has many vagal nerves and the stimulation and/or blocking therapies described herein may be applied to one or more vagal nerves, which may reside at any location of a patient (e.g., lumbar, thoracic, etc.). Further, a sequence of stimulations and/or blocking therapies may be applied to different nerves or portions of nerves. For example, a low frequency stimulation may be applied to a first nerve and a high frequency blockade may be applied to a second nerve.

Figure 2:
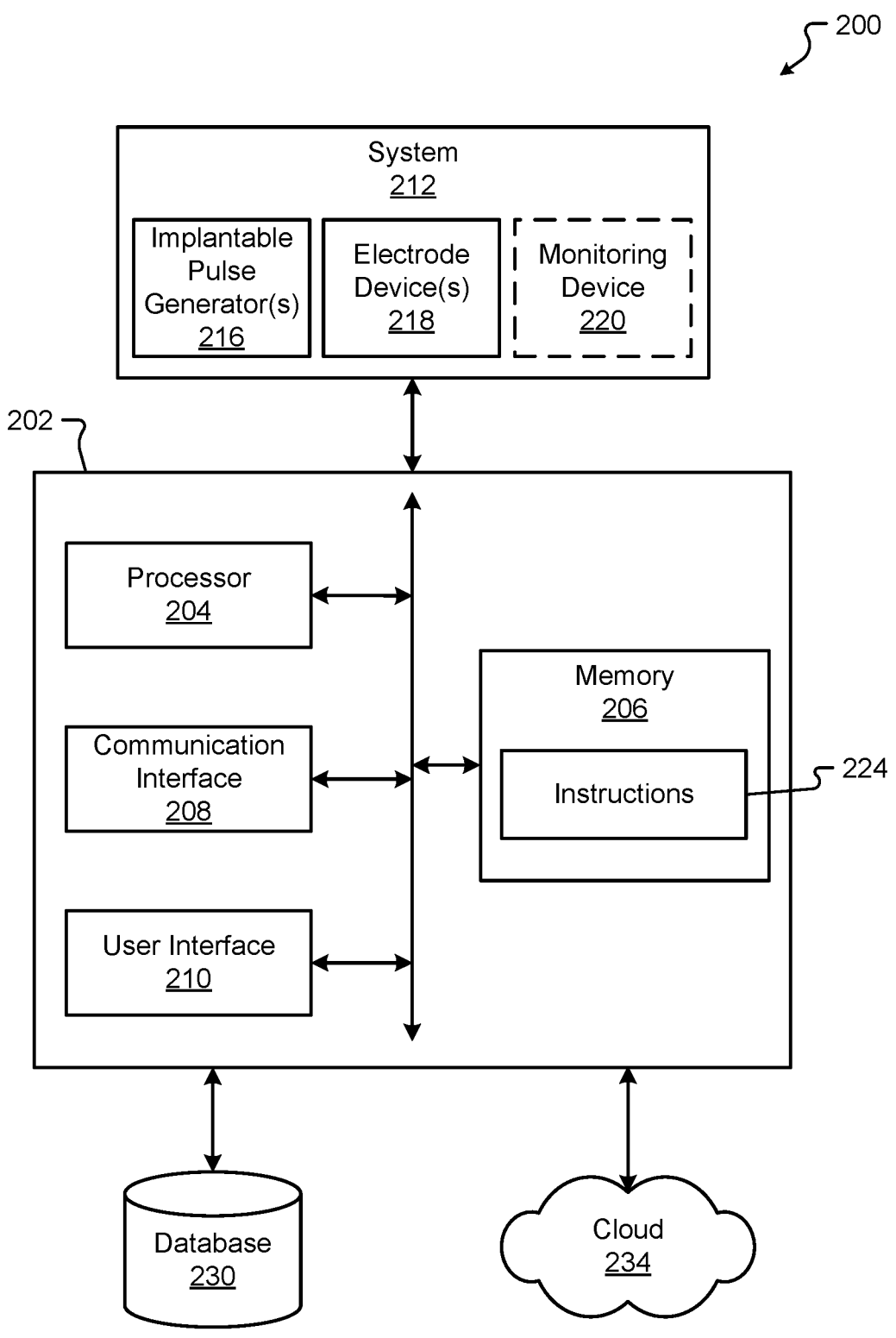
FIG. 2 is a block diagram of a system according to at least one embodiment of the present disclosure.

FIG. 2 depicts a block diagram of a system 200 according to at least one embodiment of the present disclosure is shown. In some examples, the system 200 may implement aspects of or may be implemented by aspects of FIG. 1 as described herein. For example, the system 200 may be used with an implantable pulse generator 216 and/or an electrode device 218, and/or carry out one or more other aspects of one or more of the methods disclosed herein. The implantable pulse generator 216 may represent an example of the device 104 or a component of the device 104 as described with reference to FIG. 1, where the electrode device 218 may represent the wires 108 and corresponding electrodes/cuff electrodes as described with reference to FIG. 1. Additionally or alternatively, the system 200 may be used with a monitoring device 220 and/or may carry out one or more other aspects of one or more of the methods disclosed herein. The monitoring device 220 may represent an example of the glucose sensor 112 as described with reference to FIG. 1 or, more generically, a monitoring device as described herein. The system 200 comprises a computing device 202, a system 212, a database 230, and/or a cloud or other network 234. Systems according to other embodiments of the present disclosure may comprise more or fewer components than the system 200. For example, the system 200 may not include one or more components of the computing device 202, the database 230, and/or the cloud 234.

The system 212 may comprise the implantable pulse generator 216 and the electrode device 218. As previously described, the implantable pulse generator 216 may be configured to generate a current, and the electrode device 218 may comprise a body and a plurality of electrodes, where the plurality of electrodes is configured to apply the current to an anatomical element. Additionally or alternatively, the system 212 may comprise the monitoring device 220 that is configured to continuously monitor glucose levels in the patient (e.g., such that the current is applied to the anatomical element based in part on the monitoring device 220 detecting decreased glucose levels in the patient). The system 212 may communicate with the computing device 202 to receive instructions such as instructions 224 for applying a current to the anatomical element, where the current is configured to adjust glucose levels of the patient. The system 212 may also provide data (such as data received from an electrode device 218 capable of recording data), which may be used to optimize the electrodes of the electrode device 218 and/or to optimize parameters of the current generated by the implantable pulse generator 216.

The computing device 202 comprises a processor 204, a memory 206, a communication interface 208, and a user interface 210. Computing devices according to other embodiments of the present disclosure may comprise more or fewer components than the computing device 202. In some examples, the user interface 210 may be an example of the user interface 124 as described with reference to FIG. 1. For example, the user interface 210 may be in communication with the implantable pulse generator 216, the electrode device 218, and/or the monitoring device 220. Additionally, the user interface 210 may include a first element configured to display information associated with the patient, a second element configured to receive inputs for programming parameters of the current, and a third element configured to display diagnostic information associated with applying the current to the anatomical element. Accordingly, the implantable pulse generator 216 may apply the current to the anatomical element of the patient via the plurality of electrodes of the electrode device based on one or more inputs entered via the user interface 210.

The processor 204 of the computing device 202 may be any processor described herein or any similar processor. The processor 204 may be configured to execute instructions 224 stored in the memory 206, which instructions may cause the processor 204 to carry out one or more computing steps utilizing or based on data received from the system 212, the database 230, and/or the cloud 234.

The memory 206 may be or comprise RAM, DRAM, SDRAM, other solid-state memory, any memory described herein, or any other tangible, non-transitory memory for storing computer-readable data and/or instructions. The memory 206 may store information or data useful for completing, for example, any steps of the method 600 described herein, or of any other methods. The memory 206 may store, for example, instructions and/or machine learning models that support one or more functions of the system 212. For instance, the memory 206 may store content (e.g., instructions 224 and/or machine learning models) that, when executed by the processor 204, cause the electrode device(s) 218 to apply a current to respective vagal trunks of the patient to regulate insulin production in the patient.

Content stored in the memory 206, if provided as in instruction, may, in some embodiments, be organized into one or more applications, modules, packages, layers, or engines. Alternatively or additionally, the memory 206 may store other types of content or data (e.g., machine learning models, artificial neural networks, deep neural networks, etc.) that can be processed by the processor 204 to carry out the various method and features described herein. Thus, although various contents of memory 206 may be described as instructions, it should be appreciated that functionality described herein can be achieved through use of instructions, algorithms, and/or machine learning models. The data, algorithms, and/or instructions may cause the processor 204 to manipulate data stored in the memory 206 and/or received from or via the system 212, the database 230, and/or the cloud 234.

The computing device 202 may also comprise a communication interface 208. The communication interface 208 may be used for receiving data (for example, data from an electrode device 218 capable of recording data) or other information from an external source (such as the system 212, the database 230, the cloud 234, and/or any other system or component not part of the system 200), and/or for transmitting instructions, images, or other information to an external system or device (e.g., another computing device 202, the system 212, the database 230, the cloud 234, and/or any other system or component not part of the system 200). The communication interface 208 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, Zig-Bee, and so forth). In some embodiments, the communication interface 208 may be useful for enabling the device 202 to communicate with one or more other processors 204 or computing devices 202, whether to reduce the time needed to accomplish a computing-intensive task or for any other reason.

The computing device 202 may also comprise one or more user interfaces 210. The user interface 210 may be or comprise a keyboard, mouse, trackball, monitor, television, screen, touchscreen, and/or any other device for receiving information from a user and/or for providing information to a user. The user interface 210 may be used, for example, to receive a user selection or other user input regarding any step of any method described herein. Notwithstanding the foregoing, any required input for any step of any method described herein may be generated automatically by the system 200 (e.g., by the processor 204 or another component of the system 200) or received by the system 200 from a source external to the system 200. In some embodiments, the user interface 210 may be useful to allow a surgeon or other user to modify instructions to be executed by the processor 204 according to one or more embodiments of the present disclosure, and/or to modify or adjust a setting of other information displayed on the user interface 210 or corresponding thereto.

Although the user interface 210 is shown as part of the computing device 202, in some embodiments, the computing device 202 may utilize a user interface 210 that is housed separately from one or more remaining components of the computing device 202. In some embodiments, the user interface 210 may be located proximate one or more other components of the computing device 202, while in other embodiments, the user interface 210 may be located remotely from one or more other components of the computer device 202. In some examples, the user interface 210 may be run on a UE that is accessible by the patient, a clinician, or both. For example, the UE may be a tablet device, a smartphone, a laptop, or another device not explicitly listed herein. Additionally or alternatively, the user interface 210 may be run on equipment owned by an institution, such as a hospital or clinic.

Though not shown, the system 200 may include a controller, though in some embodiments the system 200 may not include the controller. The controller may be an electronic, a mechanical, or an electro-mechanical controller. The controller may comprise or may be any processor described herein. The controller may comprise a memory storing instructions for executing any of the functions or methods described herein as being carried out by the controller. In some embodiments, the controller may be configured to simply convert signals received from the computing device 202 (e.g., via a communication interface 208) into commands for operating the system 212 (and more specifically, for actuating the implantable pulse generator 216 and/or the electrode device 218). In other embodiments, the controller may be configured to process and/or convert signals received from the system 212. Further, the controller may receive signals from one or more sources (e.g., the system 212) and may output signals to one or more sources.

The database 230 may store information such as patient data, results of a stimulation and/or blocking procedure, stimulation and/or blocking parameters, current parameters, electrode parameters, etc. The database 230 may be configured to provide any such information to the computing device 202 or to any other device of the system 200 or external to the system 200, whether directly or via the cloud 234. In some embodiments, the database 230 may be or comprise part of a hospital image storage system, such as a picture archiving and communication system (PACS), a health information system (HIS), and/or another system for collecting, storing, managing, and/or transmitting electronic medical records.

The cloud 234 may be or represent the Internet or any other wide area network. The computing device 202 may be connected to the cloud 234 via the communication interface 208, using a wired connection, a wireless connection, or both. In some embodiments, the computing device 202 may communicate with the database 230 and/or an external device (e.g., a computing device) via the cloud 234.

The system 200 or similar systems may be used, for example, to carry out one or more aspects of any of the method 600 as described herein. The system 200 or similar systems may also be used for other purposes.

FIG. 3 depicts a first element 300 of a user interface according to at least one embodiment of the present disclosure. In some examples, the first element 300 may implement aspects of or may be implemented by aspects of FIGS. 1-2 as described herein. For example, the first element 300 may be a tab, window, screen, panel, or different type of element of a user interface, such as the user interface 124 as described with reference to FIG. 1 or the user interface 210 as described with reference to FIG. 2. Additionally, the first element 300 may be configured to display basic information associated with the patient.

In some examples, the first element 300 may include a plurality of editable fields configured for entering the basic information associated with the patient. For example, the basic information may include, but is not limited to a name of the patient, a gender of the patient, a medical record number associated with the patient, a birthdate of the patient, a date that the implantable pulse generator described herein is implanted in the patient, a clinic name associated with the patient, a name of a physician associated with the patient, notes from a clinician, or a combination thereof.

Additionally, the first element 300 may include a selectable window comprising a plurality of laboratory test options associated with the patient. Accordingly, the patient or a clinician may select a first laboratory test from the plurality of laboratory test options in the selectable window. Subsequently, a processor (e.g., the computing device 202 and/or the processor 204 as described with reference to FIG. 2) may receive this selection and may retrieve results of the first laboratory test for the patient based on the received selection. For example, a database (e.g., the database 230 and/or the cloud 234 as described with reference to FIG. 2) may store results associated with each of the plurality of laboratory test options for the patient. After the results have been retrieved, the results of the first laboratory test (e.g., or any selected test) may be displayed within the first element 300 (e.g., in a lower right area of the first element 300).

FIG. 4 depicts a second element 400 of a user interface according to at least one embodiment of the present disclosure. In some examples, the second element 400 may implement aspects of or may be implemented by aspects of FIGS. 1-3 as described herein. For example, the second element 400 may be a tab, window, screen, panel, or different type of element of a user interface, such as the user interface 124 as described with reference to FIG. 1 or the user interface 210 as described with reference to FIG. 2. Additionally, the second element 400 may be configured to receive inputs for programming parameters of a current to be applied to an anatomical element as part of the neuromodulation therapy (e.g., stimulation/block therapy) described herein.

In some examples, the second element 400 may include a plurality of selectable parameters for configuring parameters of the neuromodulation therapy (e.g., how the current is to be applied to the anatomical element). For example, the plurality of selectable parameters may include a stimulation pattern, a waveform of the current, a stimulation frequency, a block frequency, or a combination thereof. In some examples, a clinician may input a plurality of parameters for applying the current to the anatomical element based on the plurality of selectable parameters. Subsequently, a processor (e.g., the computing device 202 and/or the processor 204 as described with reference to FIG. 2) may receive the plurality of parameters and may transmit the received plurality of parameters to an implantable pulse generator for applying the current to the anatomical element according to the plurality of parameters.

Additionally, the second element 400 may include a plurality of buttons (e.g., a button group) associated with determining optimizations for applying the neuromodulation therapy (e.g., optimization for applying the current to the anatomical element to achieve a desired glycemic response in the patient). For example, the plurality of buttons may include a first button for downloading data from the implantable pulse generator, a second button for running a machine learning algorithm configured to determine optimal parameters for applying the current, a third button for running a diagnostic test of the implantable pulse generator, and a fourth button for generating a set of growth curves associated with applying the current to the anatomical element. In some examples, the clinician may use the downloaded data (e.g., from the first button), results of the diagnostic test (e.g., from the third button), and/or the growth curves (e.g., from the fourth button) to determine which parameters to select from the plurality of selectable parameters. Additionally or alternatively, the clinician may use the third button to run the machine learning algorithm to determine optimal parameters for the current to achieve a desired glycemic response.

Additionally, the second element 400 may include a feedback window configured to display recommended parameters for the neuromodulation therapy (e.g., recommended parameters for applying the current to the anatomical element). In some examples, the recommended parameters may be displayed based on a user (e.g., the clinician) interacting with (e.g., clicking or tapping) the second button for running the machine learning algorithm configured to determine the optimal parameters. In some examples, the plurality of parameters input into the plurality of selectable parameters may correspond to the recommended parameters displayed in the feedback window. That is, the clinician may select the parameters for applying the current to the anatomical element based on an output of the machine learning algorithm displayed in the feedback window.

Additionally, the second element 400 may include an emergency pause button that, when selected by a user, is configured to initiate a stopping procedure. In some examples, the stopping procedure may include stopping the neuromodulation therapy (e.g., stopping the current from being applied to the anatomical element). For example, the processor (e.g., the computing device 202 and/or the processor 204 as described with reference to FIG. 2) may receive an input corresponding to the user selecting the emergency pause button to initiate the stopping procedure. Subsequently, the processor may transmit instructions to the implantable pulse generator to stop the neuromodulation therapy and stop applying the current to the anatomical element based on receiving the input. Additionally, the functionality of the emergency pause button may also include a double tap feature (e.g., the user double-clicking or double tapping the emergency pause button) to resume the neuromodulation therapy (e.g., text in the second element 400 may change to indicate a change in state of the neuromodulation therapy).

Figure 5:
FIG. 5 is a third element of a user interface according to at least one embodiment of the present disclosure.

FIG. 5 depicts a third element 500 of a user interface according to at least one embodiment of the present disclosure. In some examples, the third element 500 may implement aspects of or may be implemented by aspects of FIGS. 1-4 as described herein. For example, the third element 500 may be a tab, window, screen, panel, or different type of element of a user interface, such as the user interface 124 as described with reference to FIG. 1 or the user interface 210 as described with reference to FIG. 2. Additionally, the third element 500 may be configured to display diagnostic information associated with applying a current to an anatomical element as described herein.

In some examples, the third element 500 may include a window comprising a plurality of selectable time windows. Additionally, the third element 500 may include a plurality of fields displaying the diagnostic information associated with applying the current to the anatomical element. For example, the plurality of fields may include a log of a number of times the device (e.g., implantable pulse generator) has activated as per a closed loop algorithm, an average duration of each episode of the neuromodulation therapy being applied, and an average time required from a glycemic peak to recovery in a desired range. Additionally, the diagnostic information may include information associated with a duty cycle of applying the current to the anatomical element, efficacy measures of how applying the current to the anatomical element achieves a desired glycemic response in the patient, and other measures related to glycemic control.

In some examples, the diagnostic information may be generated based on a selection from the plurality of selectable time windows. For example, a processor (e.g., the computing device 202 and/or the processor 204 as described with reference to FIG. 2) may receive a time window selection from the plurality of selectable time windows. Subsequently, the processor may generate the diagnostic information to display in the plurality of fields based on the time window selection and may display the generated diagnostic information in the plurality of fields.

Additionally, the third element 500 may include a graphical display configured to display data associated with glucose measurements received from the patient. For example, as described with reference to FIGS. 1 and 2, the system provided and described herein for applying the neuromodulation therapy may include a monitoring device (e.g., the glucose sensor 120 as described with reference to FIG. 1 or the monitoring device 220 as described with reference to FIG. 2) that is configured to continuously monitor glucose levels in the patient. Accordingly, the data associated with glucose measurements displayed in the graphical display may be generated based on measurements captured by the monitoring device.

FIG. 6 depicts a method 600 that may be used, for example, to achieve glycemic control in a patient (e.g., adjust glucose levels in the patient) using neuromodulation therapy techniques as described herein. In some examples, the method 600 may use a user interface as described herein for programming parameters of the neuromodulation therapy.

The method 600 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 600. The at least one processor may perform the method 600 by executing elements stored in a memory (such as a memory in the device 104 as described above or a control unit). The elements stored in the memory and executed by the processor may cause the processor to execute one or more steps of a function as shown in method 600. One or more portions of a method 600 may be performed by the processor executing any of the contents of memory, such as providing a stimulation/block therapy and/or any associated operations as described herein.

The method 600 comprises receive, via a user interface (e.g., the user interface 124 as described with reference to FIG. 1 or the user interface 210 as described with reference to FIG. 2), a plurality of parameters for applying a current to an anatomical element of a patient (step 604). For example, the user interface may include a plurality of elements/tabs as described with reference to FIGS. 3-5 (e.g., the first element 300, the second element 400, and the third element 500) that can be accessed to find information about the patient, to program the parameters of the current via a plurality of inputs, and to generate diagnostic information associated with applying the current. While the user interface is described herein as including three elements/tabs, the user interface may include a different number of tabs/elements than three.

The method 600 also comprises transmitting the received plurality of parameters to a device configured to apply the current to the anatomical element of the patient (e.g., the device 104 as described with reference to FIG. 1, such as an implantable pulse generator 216 as described with reference to FIG. 2, an implantable neurostimulator, etc.) (step 608). The method 600 also comprises transmitting instructions to the device to apply the current to the anatomical element based on the plurality of parameters (step 612).

The present disclosure encompasses embodiments of the method 600 that comprise more or fewer steps than those described above, and/or one or more steps that are different than the steps described above.

As noted above, the present disclosure encompasses methods with fewer than all of the steps identified in FIG. 6 (and the corresponding description of the method 600), as well as methods that include additional steps beyond those identified in FIG. 6 (and the corresponding description of the method 600). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for stimulating an anatomical element of a patient, comprising:
an implantable pulse generator configured to generate a current;
an electrode device electrically coupled to the implantable pulse generator, the electrode device comprising a plurality of electrodes configured for placement on or around an anterior sub diaphragmatic hepatic vagal trunk of a patient to enable the current to be applied thereto;
a user interface in communication with the implantable pulse generator, the electrode device, or both, wherein the user interface comprises a first element configured to display information associated with the patient, a second element configured to receive one or more inputs for programming parameters of the current, and a third element configured to display diagnostic information associated with applying the current to the anterior sub diaphragmatic hepatic vagal trunk to upregulate neural activity thereof;
a processor; and
a memory storing data for processing by the processor, wherein the data, when processed, causes the processor to:
transmit instructions to the implantable pulse generator to adjust glucose levels in the patient by applying the current to the anterior sub diaphragmatic hepatic vagal trunk of the patient via the plurality of electrodes of the electrode device based at least in part on the one or more inputs entered via the user interface to upregulate neural activity of the anterior sub diaphragmatic hepatic vagal trunk of the patient.

2. The system of claim 1, wherein the memory stores further data for processing by the processor that, when processed, causes the processor to:
transmit the instructions to the implantable pulse generator to apply the current to the anterior sub diaphragmatic hepatic vagal trunk of the patient to achieve a desired glycemic response in the patient.

3. The system of claim 1, wherein the first element of the user interface comprises:
a plurality of editable fields configured for entering a name of the patient, a gender of the patient, a medical record number associated with the patient, a birthdate of the patient, a date that the implantable pulse generator is implanted in the patient, a clinic name associated with the patient, a name of a physician associated with the patient, notes from a clinician, or a combination thereof; and a selectable window comprising a plurality of laboratory test options associated with the patient.

4. The system of claim 3, wherein the memory stores further data for processing by the processor that, when processed, causes the processor to:
receive a selection of a first laboratory test from the plurality of laboratory test options in the selectable window;
retrieve, via a database storing results associated with each of the plurality of laboratory test options for the patient, results of the first laboratory test for the patient based at least in part on the received selection; and
display the retrieved results of the first laboratory test within the first element of the user interface.

5. The system of claim 1, wherein the second element of the user interface comprises:
a plurality of selectable parameters for configuring how the current is to be applied to the anterior sub diaphragmatic hepatic vagal trunk, wherein the plurality of selectable parameters comprises a stimulation pattern, a waveform of the current, a frequency of the current, or a combination thereof;
a plurality of buttons associated with determining optimizations for applying the current to the anterior sub diaphragmatic hepatic vagal trunk to achieve a desired glycemic response in the patient, wherein the plurality of buttons comprises a first button for downloading data from the implantable pulse generator, a second button for running a machine learning algorithm configured to determine optimal parameters for applying the current, a third button for running a diagnostic test of the implantable pulse generator, and a fourth button for generating a set of growth curves associated with applying the current to the anterior sub diaphragmatic hepatic vagal trunk;
a feedback window configured to display recommended parameters for applying the current to the anterior sub diaphragmatic hepatic vagal trunk, wherein the recommended parameters are displayed based at least in part on a user interacting with the second button for running the machine learning algorithm configured to determine the optimal parameters; and
an emergency pause button that, when selected by a user, is configured to initiate a stopping procedure, wherein the stopping procedure comprises stopping a neuromodulation therapy that includes applying the current to the anterior sub diaphragmatic hepatic vagal trunk.

6. The system of claim 5, wherein the memory stores further data for processing by the processor that, when processed, causes the processor to:
receive a plurality of parameters for applying the current to the anatomical element based at least in part on the plurality of selectable parameters; and
transmit the received plurality of parameters to the implantable pulse generator, wherein the current is applied to the anatomical element according to the plurality of parameters.

7. The system of claim 6, wherein the plurality of parameters corresponds to the recommended parameters displayed in the feedback window.

8. The system of claim 1, wherein the plurality of electrodes comprises:
a first set of electrodes for applying the current to the anterior sub diaphragmatic hepatic vagal trunk of the patient as a first current; and a second set of electrodes configured for placement on or around a posterior sub diaphragmatic celiac vagal trunk of the patient, and wherein the memory stores further data for processing by the processor that, when processed, causes the processor to transmit the instructions to the implantable pulse generator to adjust glucose levels in the patient by:

applying a second current via the second set of electrodes to the posterior sub diaphragmatic celiac vagal trunk of the patient to downregulate neural activity thereof.

9. The system of claim 1, wherein the third element of the user interface comprises:

a window comprising a plurality of selectable time windows;

a plurality of fields displaying the diagnostic information associated with applying the current to the anterior sub diaphragmatic hepatic vagal trunk, wherein the diagnostic information comprises information associated with a duty cycle of applying the current to the anterior sub diaphragmatic hepatic vagal trunk, efficacy measures of how applying the current to the anterior sub diaphragmatic hepatic vagal trunk achieves a desired glycemic response in the patient, and other measures related to glycemic control; and a graphical display configured to display data associated with glucose measurements received from the patient.

10. The system of claim 9, wherein the memory stores further data for processing by the processor that, when processed, causes the processor to:

receive a time window selection from the plurality of selectable time windows;

generate the diagnostic information to display in the plurality of fields based at least in part on the time window selection; and display the generated diagnostic information in the plurality of fields.

11. The system of claim 9, further comprising:

a monitoring device configured to continuously monitor glucose levels in the patient, wherein the data associated with glucose measurements displayed in the graphical display are generated based at least in part on measurements captured by the monitoring device.

12. The system of claim 1, wherein the user interface is run on a user equipment (UE) that is accessible by the patient, a clinician, or both.

13. A system for stimulating an anatomical element of a patient, comprising:

an implantable pulse generator configured to generate a current;

an electrode device comprising:

a body; and one or more electrodes disposed on the body and configured to apply the current to a posterior sub diaphragmatic celiac vagal trunk, or an anterior sub diaphragmatic hepatic vagal trunk, of a patient;

a user interface in communication with the implantable pulse generator, the electrode device, or both, wherein the user interface comprises a first element configured to display information associated with the patient, a second element configured to receive one or more inputs for programming parameters of the current, and a third element configured to display diagnostic information associated with applying the current to the posterior sub diaphragmatic celiac vagal trunk, or the anterior sub diaphragmatic hepatic vagal trunk, of the patient;

a processor; and a memory storing data for processing by the processor, wherein the data, when processed, causes the processor to:

transmit instructions to the implantable pulse generator to adjust glucose levels in the patient by applying the current to the anatomical sub diaphragmatic celiac vagal trunk, or the anterior sub diaphragmatic hepatic vagal trunk, of the patient via the one or more electrodes of the electrode device based at least in part on the one or more inputs entered via the user interface to downregulate neural activity of the posterior sub diaphragmatic celiac vagal trunk, or upregulate neural activity of the anterior sub diaphragmatic hepatic vagal trunk, of the patient.

14. The system of claim 13, wherein the memory stores further data for processing by the processor that, when processed, causes the processor to:

transmit the instructions to the implantable pulse generator to apply the current to the posterior sub diaphragmatic celiac vagal trunk, or the anterior sub diaphragmatic hepatic vagal trunk, of the patient to achieve a desired glycemic response in the patient.

15. The system of claim 13, wherein the first element of the user interface comprises:

a plurality of editable fields configured for entering a name of the patient, a gender of the patient, a medical record number associated with the patient, a birthdate of the patient, a date that the implantable pulse generator is implanted in the patient, a clinic name associated with the patient, a name of a physician associated with the patient, notes from a clinician, or a combination thereof; and a selectable window comprising a plurality of laboratory test options associated with the patient.

16. The system of claim 13, wherein the second element of the user interface comprises:

a plurality of selectable parameters for configuring how the current is to be applied to the posterior sub diaphragmatic celiac vagal trunk, or the anterior sub diaphragmatic hepatic vagal trunk, wherein the plurality of selectable parameters comprises a stimulation pattern, a waveform of the current, a stimulation frequency, a block frequency, or a combination thereof;

a plurality of buttons associated with determining optimizations for applying the current to the posterior sub diaphragmatic celiac vagal trunk, or the anterior sub diaphragmatic hepatic vagal trunk, to achieve a desired glycemic response in the patient, wherein the plurality of buttons comprises a first button for downloading data from the implantable pulse generator, a second button for running a machine learning algorithm configured to determine optimal parameters for applying the current, a third button for running a diagnostic test of the implantable pulse generator, and a fourth button for generating a set of growth curves associated with applying the current to the posterior sub diaphragmatic celiac vagal trunk, or the anterior sub diaphragmatic hepatic vagal trunk;

a feedback window configured to display recommended parameters for applying the current to the posterior sub diaphragmatic celiac vagal trunk, or the anterior sub diaphragmatic hepatic vagal trunk, wherein the recommended parameters are displayed based at least in part on a user interacting with the second button for running the machine learning algorithm configured to determine the optimal parameters; and an emergency pause button that, when selected by a user, is configured to initiate a stopping procedure, wherein the stopping procedure comprises stopping a neuromodulation therapy that includes applying the current to the posterior sub diaphragmatic celiac vagal trunk, or the anterior sub diaphragmatic hepatic vagal trunk.

17. The system of claim 13, wherein the third element of the user interface comprises:

a window comprising a plurality of selectable time windows;

a plurality of fields displaying the diagnostic information associated with applying the current to the posterior sub diaphragmatic celiac vagal trunk, or the anterior sub diaphragmatic hepatic vagal trunk, wherein the diagnostic information comprises information associated with a duty cycle of applying the current to the posterior sub diaphragmatic celiac vagal trunk, or the anterior sub diaphragmatic hepatic vagal trunk, or the anterior sub diaphragmatic hepatic vagal trunk, efficacy measures of how applying the current to the posterior sub diaphragmatic celiac vagal trunk, or the anterior sub diaphragmatic hepatic vagal trunk, achieves a desired glycemic response in the patient, and other measures related to glycemic control; and a graphical display configured to display data associated with glucose measurements received from the patient.

18. The system of claim 13, wherein the user interface is run on a user equipment (UE) that is accessible by the patient, a clinician, or both.

19. A system for stimulating an anatomical element of a patient, comprising:

an implantable pulse generator configured to generate a current;

an electrode device electrically coupled to the implantable pulse generator, the electrode device comprising:

a first set of one or more electrodes configured for placement on or around an anterior sub-diaphragmatic hepatic vagal trunk of a patient;

a second set of one or more electrodes configured for placement on or around a posterior sub-diaphragmatic celiac vagal trunk; and a user interface in communication with the implantable pulse generator, the electrode device, or both, wherein the user interface comprises a first element configured to display information associated with the patient, a second element configured to receive one or more inputs for programming parameters of the current, and a third element configured to display diagnostic information associated with glucose levels in the patient, wherein the user interface is configured to transmit the programming parameters to the implantable pulse generator, the electrode, or both, to cause:

the first set of one or more electrodes to apply a first current to the anterior sub-diaphragmatic hepatic vagal trunk of the patient; and the second set of one or more electrodes to apply a second current to the posterior sub-diaphragmatic celiac vagal trunk, to adjust glucose levels in the patient.

20. The system of claim 19, wherein the second element of the user interface is further configured to receive at least one additional input for updating the programming parameters of the current, and wherein the user interface is further configured to transmit the updated programming parameters to alter characteristics for the application of the first current, the second current, or both, to effect further adjustment to the glucose levels in the patient in furtherance of achieving a desired glycemic response in the patient.

\* \* \* \* \*